United States Patent
Sarma et al.

(10) Patent No.: US 11,753,671 B2
(45) Date of Patent: Sep. 12, 2023

(54) VISUALIZATION METHOD FOR ANALYZING ORAL BIOFILM GROWTH

(71) Applicant: Colgate-Palmolive Company, New York, NY (US)

(72) Inventors: Tulika Sarma, Hillsborough, NJ (US); Rehana Begum-Gafur, Clifton, NJ (US)

(73) Assignee: Colgate-Palmolive Company, New York, NY (US)

( * ) Notice: Subject to any disclaimer, the term of this patent is extended or adjusted under 35 U.S.C. 154(b) by 713 days.

(21) Appl. No.: 16/717,738

(22) Filed: Dec. 17, 2019

(65) Prior Publication Data

US 2020/0208193 A1 Jul. 2, 2020

Related U.S. Application Data

(60) Provisional application No. 62/784,922, filed on Dec. 26, 2018.

(51) Int. Cl.
| | |
|---|---|
| *C12Q 1/06* | (2006.01) |
| *G01B 11/06* | (2006.01) |
| *G01N 21/64* | (2006.01) |
| *G02B 21/00* | (2006.01) |

(52) U.S. Cl.
CPC ............. *C12Q 1/06* (2013.01); *G01B 11/06* (2013.01); *G01N 21/6458* (2013.01); *G02B 21/008* (2013.01)

(58) Field of Classification Search
CPC .. G02B 21/008; G02B 21/00; G02B 21/0004; G02B 21/002; G02B 21/0024; G02B 21/0052; G02B 21/0076; G02B 21/34; G02B 21/36; G02B 21/365; G02B 21/367; G01N 21/6458; G01N 1/28; G01N 1/30; C12Q 1/06; G01B 11/06
USPC ....... 359/362, 363, 368, 369, 396, 397, 398; 435/288.3, 288.4; 436/164, 166, 172, 436/805; 206/316.1, 454, 456; 73/863, 73/864.91; 356/244, 246
See application file for complete search history.

(56) References Cited

U.S. PATENT DOCUMENTS

| | | | |
|---|---|---|---|
| 8,778,889 B2 | 7/2014 | Leung | |
| 10,005,999 B2 | 6/2018 | Larimer et al. | |
| 10,258,551 B2 | 4/2019 | Rege et al. | |
| 10,278,906 B2 | 5/2019 | Rege et al. | |
| 10,280,444 B2 | 5/2019 | Shi et al. | |
| 10,292,993 B2 | 5/2019 | Choi et al. | |
| 2018/0274905 A1 | 9/2018 | Larimer et al. | |
| 2019/0192394 A1 | 6/2019 | Rege et al. | |
| 2019/0192395 A1 | 6/2019 | Rege et al. | |

FOREIGN PATENT DOCUMENTS

| | | | |
|---|---|---|---|
| WO | 2003/095995 | 11/2003 | |
| WO | 2008/088872 | 1/2007 | |
| WO | 2011/012311 | 2/2011 | |
| WO | 2013/175172 | 11/2013 | |
| WO | WO-2016147812 A1 * | 9/2016 | ............... G01N 1/28 |
| WO | 2017/223292 | 12/2017 | |
| WO | 2017/223311 | 12/2017 | |
| WO | 2018/157368 | 9/2018 | |

OTHER PUBLICATIONS

Ployon et al., 2016, "The membrane-associated MUC1 improves adhesion of salivary MUC5B on buccal cells. Application to development of an in vitro cellular model of oral epithelium," Archives of Oral Biology 61:149-155.
Adav et al., 2010, "Stereological assessment of extracellular polymeric substances, exo-enzymes, and specific bacterial strains in bioaggregates using fluorescence experiments," Biotechnology advances 28(2):255-280.
Bar-Zeev et al., 2014, "The importance of microscopic characterization of membrane biofilms in an unconfined environment," Desalination 348:8-15.
Biel et al., 2006, "Confocal microscopy of skin in vitro and ex vivo," in: Bioengineering of the Skin: Skin Imaging and Analysis, Edition 2, pp. 51-70 [retrieved from internet] http://www.researchgate.net/profile/Roger_Wepf/publication/262183173_Confocal_microscopy_of_skin_in_vitro_and_ex_vivo/links/5590682008aed6ec4bf66045/confocal-microscopy-of-skin-in-citro-and-ex-vivo.pdf.
International Search Report and Written Opinion of the International Searching Authority in International Application No. PCT/US2019/066903, dated Apr. 8, 2020.
Nygard et al., 2011, "Confocal sample preparation guide: Preparing your sample for a straight laser light path is vital to success," retrieved from the internet: URL:http://www.uwo.ca/sci/research/biotron/pdf/microscopy/LSM_SampleGuide.pdf.
Yawata et al., 2010, "Monitoring biofilm development in a microfluidic device using modified confocal reflection microscopy," Journal of Bioscience and Bioengineering 110(3):377-380.

* cited by examiner

*Primary Examiner* — Arnel C Lavarias

(57) ABSTRACT

Methods for visualizing oral biofilm growth and methods for identifying compounds that modulate biofilm growth are provided. Biofilm samples are stained with fluorescent dyes and viewed with a confocal laser scanning microscope. Biofilm samples are in a container with a cover slip configured for viewing the biofilm sample with the confocal laser scanning microscope and the coverslip has a thickness variation of 0.02 mm or less.

22 Claims, 2 Drawing Sheets

VISUALIZATION METHOD FOR ANALYZING ORAL BIOFILM GROWTH

BACKGROUND

The mouth is colonized by a characteristic and complex microbiota that grows as diverse biofilms on all mucosal and dental surfaces. This microbiota comprises protozoa, yeasts, mycoplasmas, Archaea, and bacteria, with the latter being the most numerous and diverse group. Oral biofilms are functionally and structurally organized polymicrobial communities embedded in a polysaccharide-based extracellular matrix on mucosal and dental surfaces. Bacteria live in these organized and complex communities, which provide an environment that protects them and allows them to survive.

The biofilm formation depends on multiple factors including the variation of pH and oxygen, the surface conditions and the oral microbiota. Once established, the composition of microbial communities at a site remains relatively constant over time, and this natural balance is termed "microbial homeostasis". In general, the resident oral microbiota coexists in a harmonious relationship with the host, and makes important contributions to the normal development and general health of the host. It supports the innate and adaptive host defenses in excluding exogenous and often pathogenic micro-organisms, and is responsible for the natural development of the physiology of the host. On occasions, however, the harmonious relationship can breakdown, and disease can occur. Oral biofilms, particularly those that accumulate on teeth, gingival margin and in the gingival crevice become characterized by increased levels of pathogenic bacteria. Increases in pathogenic bacteria in oral biofilm that accumulates on teeth can lead to dental caries. Subgingival oral biofilms lead to periodontal conditions and diseases such as gingivitis and periodontitis.

Artificial biofilm models have been developed to study, in a controlled laboratory setting, oral biofilms and compositions which are useful to treat and prevent damage, conditions and diseases caused by oral biofilms that have high pathogenic bacterial loads. Three common existing static biofilm models are referred to as the Aerobic model, the ACTA (semi-anaerobic) model and the Manchester (anaerobic) model. Substrates are inoculated with one or more oral bacteria species and maintained under conditions which promote bacterial growth and biofilm formation. The oral bacteria establish biofilms which coat the substrate. The biofilm coated substrate can then be treated with active agents, formulations or dilutions of formulations to determine the impact of such treatment on the bacteria and the biofilm.

The existing biofilm models present several challenges. It is difficult to mimic the oral environment with respect to species diversity as well as the complex environment of the oral cavity. Moreover, imaging studies conducted on fixed samples provide limited information while imaging studies used to evaluate treatments are difficult to perform on live samples (in their natural hydrated state) and obtaining resulting images of good quality can be challenging.

BRIEF SUMMARY

A method for visualizing oral biofilm growth is provided. The method comprises the steps of staining a biofilm sample with fluorescent dyes and viewing the biofilm sample with a confocal laser scanning microscope. The biofilm sample is in a container with a cover slip configured for viewing the biofilm sample with the confocal laser scanning microscope. The coverslip has a thickness variation of 0.02 mm or less. Multiple Z-stacks are acquired with an objective between 10× and 100× such as 10×, 20×, 50×, 60× or 100×. Images are captured, collected, processed and saved using a computer linked with the confocal laser scanning microscope so that images from the confocal laser scanning microscope can be collected, processed and saved by the computer.

A method for identifying compounds that modulate biofilm growth is also provided. The method comprises preparing a test biofilm sample and a control biofilm sample. The test biofilm sample is prepared and maintained in contact with a test compound or composition and the control biofilm sample is prepared and maintained under the same conditions as the test biofilm sample except the control biofilm sample is prepared and maintained free of the test compound or composition. Oral biofilm growth in each of the test biofilm sample and in the control biofilm sample is visualized by staining the test biofilm sample and the control biofilm sample with fluorescent dyes. The stained test biofilm sample and the stained control biofilm sample are each viewed with a confocal laser scanning microscope. The test biofilm sample is in a container with a cover slip configured for viewing the test biofilm sample with the confocal laser scanning microscope wherein the coverslip has a thickness variation of 0.02 mm or less, and the control biofilm sample is in a container with a cover slip configured for viewing the control biofilm sample with the confocal laser scanning microscope, wherein the coverslip has a thickness variation of 0.02 mm or less. Multiple Z-stacks are acquired with an objective between 10× and 100× such as 10×, 20×, 50×, 60× or 100×. Images are captured, collected, processed and saved using a computer linked with the confocal laser scanning microscope so that images from the confocal laser scanning microscope can be collected, processed and saved by the computer. The results of visualization of the test biofilm sample and results of visualization of the control biofilm sample are compared and differences in the growth of the test biofilm sample relative to the growth of the control biofilm are identified.

DETAILED DESCRIPTION

Figure 1:
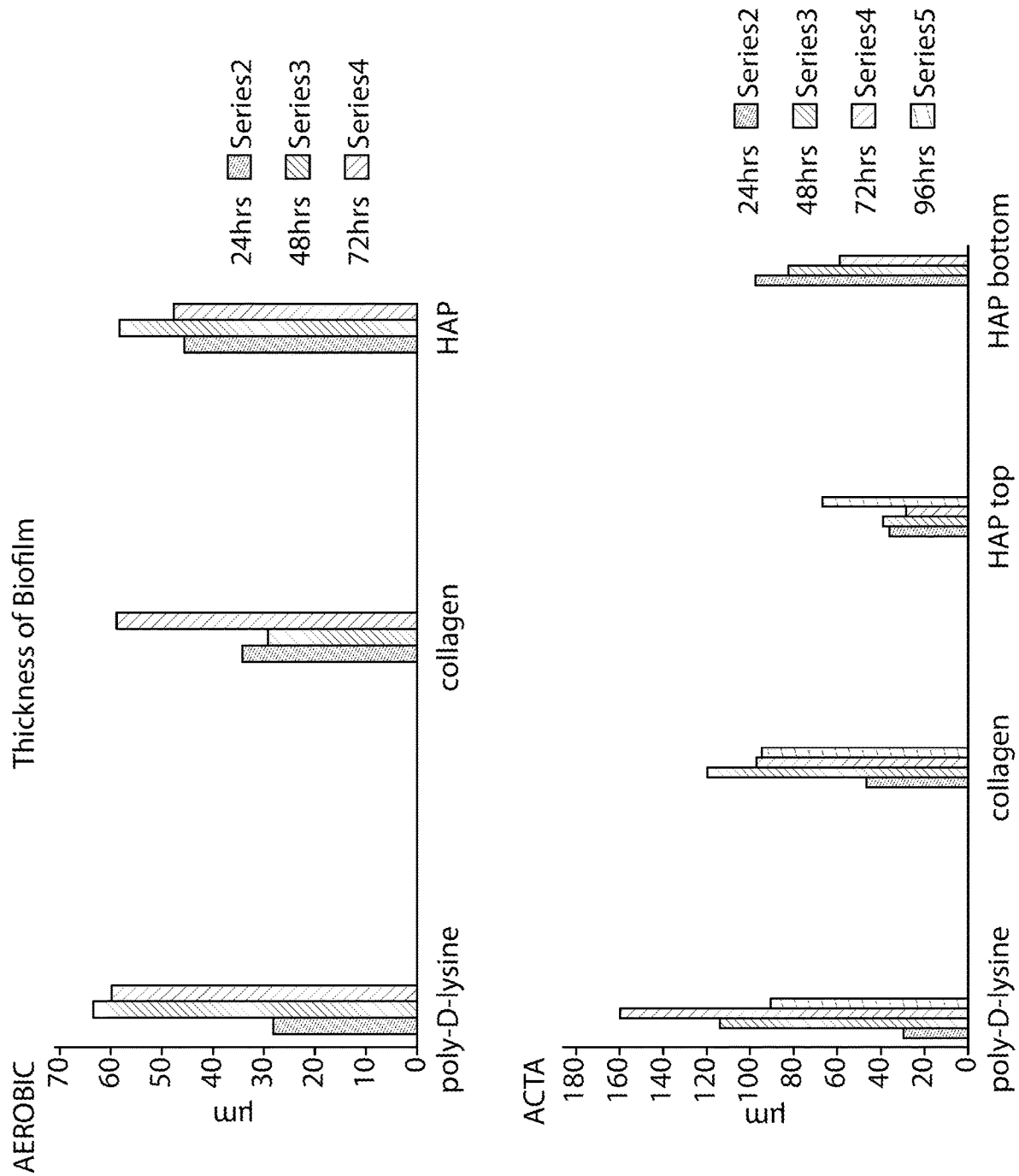
FIG. 1 shows data comparing biofilm thickness results from experiments using growing biofilms with the Aerobic and ACTA models in which three different growth surfaces were used for each model.
Figure 2A:
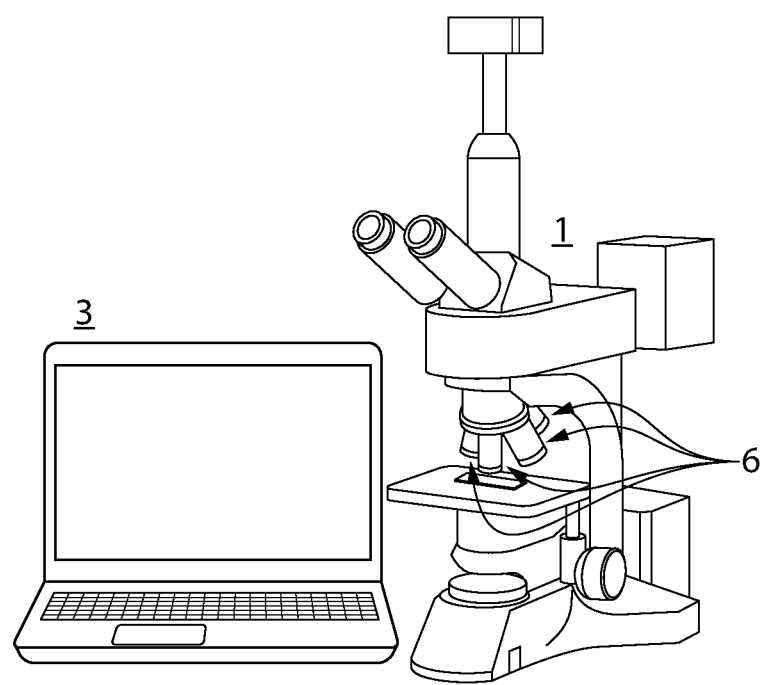
FIG. 2A is a perspective view of a computer linked with a confocal laser scanning microscope in accordance with an embodiment of the present invention.
Figure 2B:
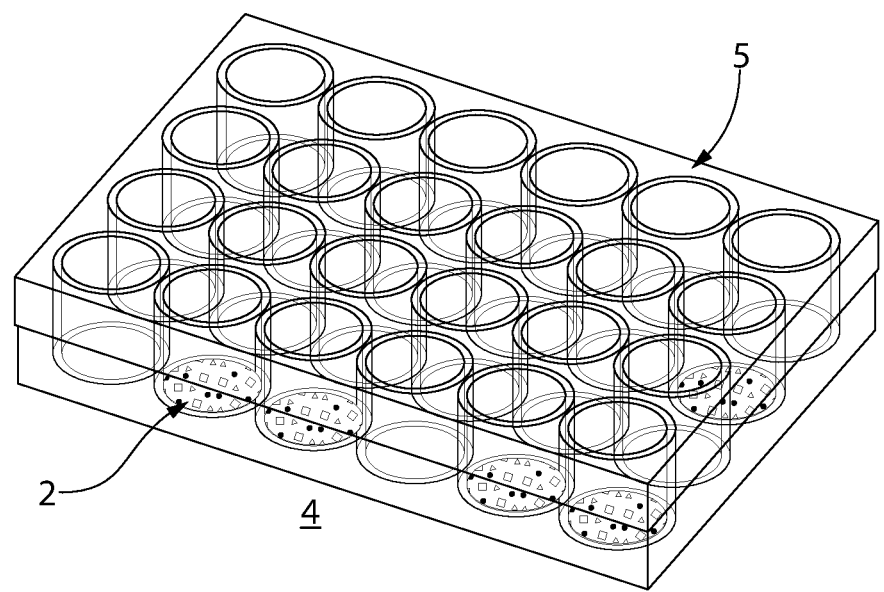
FIG. 2B is a perspective view of a glass-bottomed multi-well plate having a transparent bottom in accordance with another embodiment of the present invention.

A non-invasive method to visualize the biofilm formation and analyze bacterial viability and to evaluate the biofilm growth on different materials/substrates that are optimized for Wide-field and Confocal imaging has been established and validated. Biofilm attachment and biofilm formation of salivary inoculum can be visualized in real-time using live imaging. Biofilms can be visualized over time courses and imaging can include videos. The method can be used to visualize, establish and validate protocols that optimize biofilm growth conditions for aerobic and semi-aerobic lab models of salivary biofilm. The method allows for the development of preclinical models suitable for visualizing dynamics of biofilm formation in real-time. The method enables the study of mode of action of products and is also useful with respect to comparative studies for pre- and post-treatment effects. A method has been established for quantifying biofilm formation. Biofilm formation can be imaged and temporal dynamics of bacterial microbiota over time during biofilm formation and maturation can be recorded. Changes and break down in the bacterial community and biofilm architecture over time can be visualized and the characteristics of biofilm growth over time can be evaluated. Real-time imaging of live biofilm can used to study aspects of biofilms, such as surface specific mechanics, hydrodynamic and adhesive forces, and flow dynamics of biofilm.

A confocal laser scanning microscope (LSM) 1 isolates and collects a plane of focus from within a sample 2. The out of focus "haze" normally seen with a fluorescent sample is eliminated allowing for detection fine detail that is obscured by the haze in a non-confocal, fluorescent microscope. A stepper motor (Z drive) attached to the fine focus of the confocal LSM enables the collection of a series of images through a three-dimensional object (Z-stack). The images are captured and stored on a computer 3 attached to the confocal LSM and software can create a two- or three-dimensional reconstruction from the images. Samples can be stained with double and triple labels. Precise colocalizations can be performed because images collected with the confocal LSM microscope are collected from an optical plane within the sample.

Using laser scanning microscopy in real-time imaging of live biofilm requires acquisition of the Z-stack with precise spacing. A motorized Z-drive (piezo or motor) may be used in acquisition of the Z-stack. With respect to real-time imaging of live biofilm, confocal laser scanning microscopy has many advantages over light microscopy. In conventional (i.e., wide-field) fluorescence microscopy the entire specimen is flooded evenly in light from a light source. All parts of the specimen in the optical path are excited at the same time and the resulting fluorescence is detected by the microscope's photodetector or camera including a large unfocused background part. Light from out-of-focus structures blurs in-focus information. In addition, image quality is degraded by aberrations inherent to optics. Moreover, image quality in light microscopy is degraded by refraction; light passes through materials with many different refractive indices (glass, sample, mounting media, immersion, air). Other disadvantages of light microscopy include low contrast and low resolution, especially in the Z-direction. Use of laser scanning microscopy using a confocal laser scanning microscope (LSM) provides better images and fewer shortcomings.

A confocal laser scanning microscope uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. In confocal laser scanning microscope, a sensitive detector, usually a photomultiplier tube (PMT) or avalanche photodiode, can transform a light signal into an electrical one that is recorded by a computer. In some embodiments, the confocal laser scanning microscope Nikon is a confocal LSM such as Nikon A1+, Nikon A1 MP+, Nikon A1 R MP+, Nikon A1 R HD, Nikon A1 HD25 confocal microscope, the Nikon A1 R HD25 confocal microscope, the multiphoton confocal microscope the Nikon C2+ confocal microscope system. In some embodiments, microscope is a Nikon Eclipse Ti inverted microscope. In some embodiments, multiple Z-stacks are acquired with a 10× to 100× objective. In some embodiments, multiple Z-stacks are acquired with a 10× to 60× objective. In some embodiments, multiple Z-stacks are acquired with a 10× to 50× objective. In some embodiments, multiple Z-stacks are acquired with a 15× to 25× objective. In some embodiments, multiple Z-stacks are acquired with a 10× objective, or a 15× objective, or a 20× objective, a 25× objective, or a 40× objective, or a 50× objective, or a 60× objective or a 100× objective. Images are captured, collected, processed and saved using Nikon software such as Nikon Imaging Software NIS Elements Confocal microscope imaging software, such as version 5.0.

As only one point in the sample is illuminated at a time, 2D or 3D imaging requires scanning over a regular raster (i.e., a rectangular pattern of parallel scanning lines) in the specimen. The beam is scanned across the sample in the horizontal plane by using one or more (servo controlled) oscillating mirrors. This scanning method usually has a low reaction latency and the scan speed can be varied. Slower scans provide a better signal-to-noise ratio, resulting in better contrast and higher resolution.

The achievable thickness of the focal plane is defined mostly by the wavelength of the used light divided by the numerical aperture of the objective lens, but also by the optical properties of the specimen. The thin optical sectioning that is possible makes these types of microscopes particularly good at 3D imaging and surface profiling of samples. Successive slices that make up a 'z-stack' can be processed by certain software to create a 3D image. Direct, noninvasive, serial optical sectioning can be done on intact, thick, live biofilm. The successive slices that make up a 'z-stack' can also be merged into a 2D stack (predominately the maximum pixel intensity is taken, other common methods include using the standard deviation or summing the pixels). In addition to creation of 2D and 3D images, post processing of collected data can be used to make time-lapsed movies/video and to perform volumetric analysis of biofilm such as visual representation and structural integrity of Live (green/Syto9) and Dead (red/PI) population of biofilm-forming bacteria and measurement of biofilm thickness.

Biofilms can be stained with fluorescent stains that distinguish live from dead material. For example, in some embodiments, biofilms are stained LIVE/DEAD BacLight Viability Kit (Syto 9 and PI, Invitrogen). Other reagents and techniques that use fluorescence may also be employed in visualization methods that use laser scanning microscopy. Several factors are considered when optimizing fluorescence imaging parameters. Resolution quality corresponds to pixel size and the number of pixels. Detection of molecules in sub-cellular structures is achieved with optimized resolution. Observation of dynamic live processes requires optimized speed with respect to Hz/second and signal/noise. Sensitivity, which allows for detection of weak labels in photosensitive samples, is optimized by factors such as low noise, quantum efficiency and pixel size.

Typically, the specimen is in a dish or well of a multi-well plate 4 which has a cover slip 5. The thickness of the coverslip is important for optimal image quality. Use of a proper cover slip is important. An objective lens is designed for a cover slip with an ideal thickness. Using the wrong coverslip may have serious implications for image intensity and quality. This is particularly true for objectives 6 with Numerical Aperture (NA) above 0.4 and when the sample is very close (e.g. adhered to or in contact with) the coverslip. Coverslip thicknesses are shown in Table 1. Most objectives are designed to use #1.5 coverslips. There is actually a surprising amount of variation in a batch of cover slips. As noted in Table 1, for cover slips with a given ideal thickness, the actual thicknesses of a batch of cover slips may fall within a relatively broad range.

TABLE 1

Cover slip thickness and variation

| Cover slip # | Ideal thickness | Range |
| --- | --- | --- |
| #0 | 100 μm | 80-130 μm |
| #1 | 150 μm | 130-170 μm |
| #1.5 | 170 μm | 160-190 μm |
| #2.0 | 220 μm | 190-250 μm |

Cover slip thickness variation significantly reduces performance. Table 2 refers to performance reduction over a range of NAs for cover slips with thickness variations of 10 μm and 20 μm.

TABLE 2

Performance reduction with cover slip thickness variation

| Numerical Aperture | 0.01 mm (10 μm) Deviation | 0.02 mm (20 μm) Deviation |
| --- | --- | --- |
| 0.30 | none | none |
| 0.45 | none | none |
| 0.70 | 2% | 8% |
| 0.85 | 19% | 57% |
| 0.95 | 55% | 71% |

Accordingly, cover slip thickness preferably has a variation of 20 μm or less, more preferably 10 μm or less.

In some embodiments, the sample is contained in a multi-well plate which has a transparent bottom that serves as cover slip. Examples of micro-well plates include Greiner Bio-One SensoPlate™ glass bottom plates. Examples include 24, 96, 384 and 1536 well glass bottom formats. Plates consist of an optically clear borosilicate glass bottom with a light path of 175+/−15 μm and a black polystyrene frame. The glass bottom allows transmission measurements in the wavelength range above 350 nm. The 175 μm thick glass bottom of the SensoPlate™ is equivalent to the light path of standard coverslips. SensoPlate™ may be pre-coated with Poly-Lysine or Collagen. Other examples of micro-well dishes include MatTek Glass Bottom Dishes (MatTek Corp, Ashland, MA), which include optical quality glass. MatTek Dish Types come in various sizes such as 35 mm dishes which have microwell diameters of 7 mm, 10 mm, 14 mm and 20 mm, 50 mm dishes which have microwell diameters of 14 mm and 30 mm, 60 mm dishes which have microwell diameters of 20 mm and 30 mm, and 100 mm dishes which have microwell diameter of 30 mm. MatTek Dish Types come in various glass thickness corresponding to coverslip sizes, for example 35 mm dishes come with glass thicknesses of No. 0, No. 1.0, No. 1.5, No. 0.170, and No. 2.0 (Grid), 50 mm dishes come with glass thicknesses of No. 0, No. 1.5, and No. 2.0 (Grid), and 60 mm dishes and 100 mm dishes come with glass thicknesses of No. 1.5. MatTek glass dishes as described here mat be Poly-d-lysine and collagen coated dishes.

Biofilm can be grown on different surfaces such as poly-D-lysine, collagen-coated or Hydroxyapatite (HAP) disks. In some embodiments, biofilm is grown on the surface of a 35 mm×0.17 mm poly-D-lysine plate. In some embodiments, biofilm is grown on the surface of a 35 mm×0.17 mm collagen-coated plates. In some embodiments, biofilm is grown on 12 mm HAP disks. In some embodiments, biofilm is grown on 0.5"×0.04-0.06 HAP disks. In some embodiments, saliva, which contains oral bacteria, is collected and incubated with a substrate (e.g. poly-D-lysine, collagen-coated or HAP disks). In some embodiments, substrate is inoculated with one or more oral bacteria species and incubated. The oral bacteria establish biofilms which coat substrate and substrate are incubated with growth media. In some embodiments, the biofilm coated substrate can then be treated with active agents, formulations or dilutions of formulations to determine the impact of such treatment on the bacteria.

Methods of visualization may be used in methods identifying compounds that modulate biofilm growth. In such methods a test biofilm sample and a control biofilm sample are prepared. The test biofilm sample and control biofilm are identical except the test biofilm sample is prepared and maintained in contact with a test compound or composition and the control biofilm sample is prepared and maintained under the same conditions as the test biofilm sample except the control biofilm sample is prepared and maintained free of the test compound or composition. Oral biofilm growth of the test biofilm sample and the control biofilm sample is visualized using the visualization methods decried herein. The test biofilm sample and the control biofilm sample are stained with fluorescent dyes then viewing with a confocal laser scanning microscope. The test biofilm sample and the control biofilm sample are in identical containers. Each container included a cover slip configured for viewing the biofilm sample with the confocal laser scanning microscope. The confocal laser scanning microscope acquires multiple Z-stacks of each of the test biofilm sample and the control biofilm sample with an objective between 10× and 100×, such as between 10× and 50× or between 15× and 25×. In some embodiments, objectives used include 15×, 20× or 25×. In some embodiments, objectives used include 10×, 20×, 60× or 100×. Images of the test biofilm sample and the control biofilm sample are captured, collected, processed and saved using a computer linked with the confocal laser scanning microscope so that images from the confocal laser scanning microscope can be collected, processed and saved by the computer. Results of visualization of the test biofilm sample are compared with results of visualization of the control biofilm sample and differences in the growth of the test biofilm sample relative to the growth of the control biofilm are identified. Differences that are identified correspond to the effect the test compound or composition has on biofilm growth.

In some embodiments, multiple test biofilm samples are used wherein different concentrations of test compound or compositions, such as serial dilutions are tested. In some embodiments, duplicate test biofilm sample and control biofilm samples are tested.

In some embodiments, the test biofilm sample and the control biofilm sample are prepared using a model selected from the group consisting of: Aerobic model, ACTA model and Manchester model. In some embodiments, the test biofilm sample and the control biofilm sample are grown on a growth surface selected from the group consisting of: a HAP disk, a poly-lysine coated plate and a collagen-coated plate. In some embodiments, the test biofilm sample and the control biofilm sample are stained with a mixture of SYTO® 9 green-fluorescent nucleic acid stain and red-fluorescent nucleic acid stain propidium iodide. In some embodiments, the cover slip has a thickness variation of 0.02 or less. In some embodiments, the cover slip has a thickness variation of 0.01 or less. In some embodiments, the multiple Z-stacks are acquired with a 20× objective for the test biofilm sample and the control biofilm sample. In some embodiments, each test biofilm sample and each control biofilm sample is visualized multiple times at different time points. In some embodiments, each test biofilm sample and each control biofilm sample is visualized daily for 1-5 days. In some embodiments, the images of the test biofilm sample and the control biofilm sample that are collected are used to generate a time lapse video. In some embodiments, the images of the test biofilm sample and the control biofilm sample that are collected are used to generate 3D-biofilm images. In some embodiments, the images of the test biofilm sample and the control biofilm sample that are collected are used to perform volumetric analysis of the biofilm sample. In some embodiments, the images of the test biofilm sample and the control biofilm sample that are collected are used to measure biofilm thickness. If, for example, the test biofilm sample is found to grow more slowly or grows to a smaller maximum thickness compared to control, such data indicates the test compound or composition inhibits biofilm growth.

EXAMPLES

Example 1

The Manchester Biofilm Model is an anaerobic model. HAP disks are inoculated with 1 ml human saliva/1 ml artificial saliva+0.1% sucrose and incubated for 24 hr, resulting in biofilm formation. The biofilm coated HAP disk is treated by adding 1 ml 10% toothpaste slurry. After 10 min exposure, the planktonic phase removed. Every day for 8 days, 2 ml artificial saliva +0.1% sucrose are added and treatment of the HAP disks with the toothpaste slurry is performed once per day. HAP disks are analyzed at days 2, 4, and 8 days by plating. Day 2 is baseline. Efficacy is evaluated at Day 8. Dilutions are plated in triplicate.

Example 2

LIVE/DEAD® BacLight™ Bacterial Viability Kit (ThermoFisher Scientific Inc) utilizes mixtures of SYTO® 9 green-fluorescent nucleic acid stain and the red-fluorescent nucleic acid stain, propidium iodide. These stains differ both in their spectral characteristics and in their ability to penetrate healthy bacterial cells. The excitation/emission maxima for these dyes are about 480/500 nm for SYTO 9 stain and 490/635 nm for propidium iodide.

To stain a biofilm, combine equal volumes of SYTO® 9 and propidium iodide in a microfuge tube. Add 3 μL of the dye mixture directly to the biofilm and incubate at room temperature in the dark for 15 minutes.

Example 3

Visualization of biofilms was used to study and compare biofilm growth over time. For each of three different models, biofilms were grown on three different growth surfaces. For biofilm grown using two of the three models, biofilm thickness was measured daily for 3 days. For biofilm grown using one of the three models, biofilm thickness was measured daily for 4 days. Table 3 shows details of the experiment.

TABLE 3

| Model | Growth Surfaces | Growth environment | Media | 24 hr | 48 hr | 72 hr | 96 hr |
|---|---|---|---|---|---|---|---|
| Aerobic | HAP | Aerobic | SHI | ✓ | ✓ | ✓ | |
| Aerobic | Poly-lysine | Aerobic | SHI | ✓ | ✓ | ✓ | |
| Aerobic | Collagen-coated | Aerobic | SHI | ✓ | ✓ | ✓ | |
| ACTA | HAP | Anaerobic | McBain | ✓ | ✓ | ✓ | ✓ |
| ACTA | Poly-lysine | Anaerobic | McBain | ✓ | ✓ | ✓ | ✓ |
| ACTA | Collagen-coated | Anaerobic | McBain | ✓ | ✓ | ✓ | ✓ |

Data is shown in FIG. 1. Data from experiments using the Aerobic model showed that thickness and volume (visual) increases at 48 hrs. Maximum thickness is reached at 48 hrs-60 mm. Thickness of biofilm decreases slightly at 72 hrs. The pattern of biofilm growth is very similar in biofilms grown on HAP discs and poly-D-lysine coated dishes. Data from experiments using the ACTA model showed that thickness decreases after 24 hours in biofilms grown on HAP disks whereas thickness decreases only after 96 hours in biofilms grown in poly-D-lysine coated dishes.

The invention claimed is:

1. A method for visualizing oral biofilm growth comprising the steps of:
   a) staining a biofilm sample with fluorescent dyes; and
   b) viewing the biofilm sample multiple times at different time points with a confocal laser scanning microscope wherein
      i) the biofilm sample is in a glass-bottomed multi-well plate which has a transparent bottom that serves as a cover slip configured for viewing the biofilm sample with the confocal laser scanning microscope, wherein the coverslip has a thickness corresponding to a coverslip size No. 1.5 and a thickness variation of 0.02-mm or less;
      ii) multiple Z-stacks are acquired with an objective selected from the group consisting of: 10× and 20×, and
      iii) images are captured, collected, processed and saved using a computer linked with the confocal laser scanning microscope so that images from the confocal laser scanning microscope can be collected, processed and saved by the computer.

2. The method of claim 1 wherein the coverslip has a thickness variation of 0.01 mm or less.

3. The method of claim 1 wherein the objective is 20×.

4. The method of claim 1 wherein the biofilm sample is prepared using a model selected from the group consisting of: Aerobic model, ACTA model and Manchester model.

5. The method of claim 1 wherein the biofilm sample is grown on a growth surface selected from the group consisting of: a Hydroxyapatite (HAP) disk, a poly-lysine coated plate and a collagen-coated plate.

6. The method of claim 1 wherein the biofilm is stained with a mixture of green-fluorescent nucleic acid stain and red-fluorescent nucleic acid stain propidium iodide.

7. The method of claim 1 wherein the images of the biofilm sample that are collected are used to generate a time lapse video.

8. The method of claim 1 wherein the biofilm sample is visualized daily for 1-5 days.

9. The method of claim 1 wherein the images of the biofilm sample that are collected are used to generate a 3D-biofilm image.

10. The method of claim 1 wherein the images of the biofilm sample that are collected are used to perform volumetric analysis of the biofilm sample and to measure biofilm thickness.

11. A method for identifying compounds that modulate biofilm growth comprising the step of
   a) preparing a test biofilm sample, wherein the test biofilm sample is in a test container which is a glass-bottomed multi-well plate which has a transparent bottom that serves as the test sample cover slip configured for viewing the test biofilm sample with a confocal laser scanning microscope, wherein the coverslip has a thickness corresponding to a coverslip size No. 1.5 and a thickness variation of 0.02 mm or less, and the test biofilm sample is prepared and maintained in contact with a test compound or composition;
   b) preparing a control biofilm sample, wherein the control biofilm sample is in a control container which is a control glass-bottomed multi-well plate which has a transparent bottom that serves as the control cover slip configured for viewing the control biofilm sample with the confocal laser scanning microscope, wherein the coverslip has a thickness corresponding to a coverslip size No. 1.5 and a thickness variation of 0.02 mm or less, and preparation and maintenance of the control biofilm sample and the test biofilm sample are identical except the control biofilm sample is prepared and maintained free of the test compound or composition;
   c) visualizing the test biofilm sample comprising the steps of:
      i) staining the test biofilm sample with fluorescent dyes;
      ii) viewing the test biofilm sample multiple times at different time points with the confocal laser scanning microscope wherein
         1) multiple Z-stacks are acquired with an objective selected from the group consisting of: 10× and 20×, and
         2) images of the test biofilm sample are captured, collected, processed and saved using a computer linked with the confocal laser scanning microscope so that images from the confocal laser scanning microscope can be collected, processed and saved by the computer;
   d) visualizing the control biofilm sample with the confocal laser scanning microscope comprising the steps of:
      i) staining the control biofilm sample with fluorescent dyes;
      ii) viewing the control biofilm sample multiple times at different time points with the confocal laser scanning microscope wherein
         1) multiple Z-stacks are acquired with an objective selected from the group consisting of: 10× and 20×; and
         2) images of the control biofilm sample are captured, collected, processed and saved using the computer linked with the confocal laser scanning microscope so that images from the confocal laser scanning microscope can be collected, processed and saved by the computer;
   e) comparing results of visualization of the test biofilm sample and results of visualization of the control biofilm sample and identifying differences in growth of the test biofilm sample relative to growth of the control biofilm.

12. The method of claim 11 wherein the coverslip has a thickness variation of 0.01 mm or less.

13. The method of claim 11 wherein the objective is 20×.

14. The method of claim 11 wherein the test biofilm sample and the control biofilm sample are each prepared using a model selected from the group consisting of: Aerobic model, ACTA model and Manchester model.

15. The method of claim 11 wherein the test biofilm sample and the control biofilm sample are each grown on a growth surface selected from the group consisting of: a HAP disk, a poly-lysine coated plate and a collagen-coated plate.

16. The method of claim 11 wherein the test biofilm sample and the control biofilm sample are each stained with a mixture of green-fluorescent nucleic acid stain and red-fluorescent nucleic acid stain propidium iodide.

17. The method of claim 11 wherein the images of the test biofilm sample that are collected are used to generate a time lapse video of the test biofilm sample and the images of the control biofilm sample that are collected are used to generate a time lapse video of the control biofilm sample.

18. The method of claim 11 wherein the test biofilm sample and the control biofilm sample are each visualized daily for 1-5 days.

19. The method of claim 11 wherein the images of the test biofilm sample that are collected are used to generate a 3D-biofilm image of the test biofilm sample and the images of the control biofilm sample that are collected are used to generate a 3D-biofilm image of the control biofilm sample.

20. The method of claim 11 wherein the images of the test biofilm sample that are collected are used to perform volumetric analysis of the test biofilm sample and the images of the control biofilm sample that are collected are used to perform volumetric analysis of the control biofilm sample and the images of the test biofilm sample that are collected are used to measure biofilm thickness of the test biofilm sample and the images of the control biofilm sample that are collected are used to measure biofilm thickness of the control biofilm sample.

21. The method of claim 11 wherein the images of the test biofilm sample that are collected are used to perform volumetric analysis of the test biofilm sample and the images of the control biofilm sample that are collected are used to perform volumetric analysis of the control biofilm sample or the images of the test biofilm sample that are collected are used to measure biofilm thickness of the test biofilm sample and the images of the control biofilm sample that are collected are used to measure biofilm thickness of the control biofilm sample.

22. The method of claim 1 wherein the images of the biofilm sample that are collected are used to perform volumetric analysis of the biofilm sample or to measure biofilm thickness.

* * * * *